(12) United States Patent
Adams et al.

(10) Patent No.: US 6,635,648 B2
(45) Date of Patent: Oct. 21, 2003

(54) COMBINATION THERAPY USING SYMPATHETIC NERVOUS SYSTEM ANTAGONISTS AND ENDOTHELIN ANTAGONISTS

(75) Inventors: Michael A. Adams, Kingston (CA); Jeremy W. Heaton, Gananoque (CA); Suzanne K. Bridge, Oakville (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/930,138

(22) Filed: Aug. 16, 2001

(65) Prior Publication Data

US 2003/0087911 A1 May 8, 2003

Related U.S. Application Data

(60) Provisional application No. 60/226,098, filed on Aug. 18, 2000.

(51) Int. Cl.[7] ............ A61K 31/497; A61K 31/40; A61K 31/14
(52) U.S. Cl. ............ 514/252.17; 514/422; 514/642
(58) Field of Search ............ 514/252.17, 422, 514/642

(56) References Cited

U.S. PATENT DOCUMENTS 5,538,991 A * 7/1996 Ashton et al. ............ 517/397

* cited by examiner

*Primary Examiner*—Raymond Henley, III
(74) *Attorney, Agent, or Firm*—Stephen J. Scribner; Carol Miernicki Steeg

(57) ABSTRACT

Methods are provided for preventing or inhibiting adverse cardiovascular effects associated with administration of a sympathetic nervous system antagonist in a subject, in which a subject in need thereof is administered a sympathetic nervous system antagonist and an endothelin antagonist. Methods for improving the efficacy of a sympathetic nervous system antagonist are also provided, comprising administering to a subject in need thereof a sympathetic nervous system antagonist together with an endothelin antagonist. Methods of treating prostate cancer or benign prostate hyperplasia (BPH) in a subject are also provided, in which a subject in need thereof is administered a sympathetic nervous system antagonist and an endothelin antagonist. The sympathetic nervous system antagonist may be an alpha-adrenoceptor antagonist, a ganglionic blocking agent or another inhibitor of the actions of the sympathetic nervous system.

26 Claims, 8 Drawing Sheets

COMBINATION THERAPY USING SYMPATHETIC NERVOUS SYSTEM ANTAGONISTS AND ENDOTHELIN ANTAGONISTS

RELATED APPLICATIONS

This application claims the benefit of priority of U.S. Provisional Patent Application No. 60/226,098, filed Aug. 18, 2000, the contents of which are incorporated herein by reference in their entirety.

FIELD OF THE INVENTION

This invention relates to methods and compositions for treating hypertension, endothelial abnormalities or adverse effects induced by administration of sympathetic nervous system antagonists, using endothelin antagonists in combination with sympathetic nervous system antagonists.

BACKGROUND OF THE INVENTION

The interim analysis of the Antihypertensive and Lipid-Lowering Treatment to Prevent Heart Attack Trial (ALLHAT) has seriously challenged the concept that mean arterial pressure (MAP) lowering per se is an appropriate primary therapeutic endpoint. ALLHAT is an ongoing clinical trial involving more than 40,000 patients with hypertension and at least one other coronary heart disease (CHD) risk factor. It is a randomized, double-blind, active-controlled trial to determine meaningful differences between 4 different antihypertensive agents: a diuretic, chlorthalidone; an $\alpha_1$-adrenoceptor antagonist (one type of "alpha-blocker"), doxazosin; a calcium channel blocker, amlodipine; and an angiotensin converting enzyme (ACE) inhibitor, lisinopril. Recently the published interim report of approximately 24,000 patients by the ALLHAT Data and Safety Monitoring Board (DSMB) recommended discontinuation of one of the treatment arms that involved the $\alpha_1$-adrenoceptor antagonist. The conclusions in the interim report stated that the alpha-blocker, when compared with the diuretic, was not effective in preventing cardiovascular end points i.e. it lacked equivalent impact on morbidity and mortality risks (ALLHAT Officers and Coordinators for the ALLHAT Collaborative Research Group, JAMA 2000;283(15): 1967–1975). Explicitly, the alpha-blocker arm of the study was terminated because patients had an overall 25% increase in the risk of cardiovascular events, including more than twice the risk of congestive heart failure (CHF) within the first two years of the study (ALLHAT Officers and Coordinators for the ALLHAT Collaborative Research Group, JAMA 2000;283(15): 1967–1975). These serious negative effects occurred despite the fact that the alpha-blocker had beneficial effects both on cholesterol and blood pressure control.

The decision to discontinue the alpha-blocker arm of this trial has widespread implications. In particular the results challenge the conventional assumption that the most important parameter in treatment of hypertension is the lowering of blood pressure. The negative findings from ALLHAT provide compelling evidence that the mechanism of action is a critical consideration in the selection of antihypertensive drugs, i.e., the actions of antihypertensives must be examined beyond their effect on blood pressure. The mechanisms of action of antihypertensive drugs, in general, involve inhibiting processes that are physiological regulators of blood pressure, i.e., blood volume (renin-angiotension system (RAS) inhibitors and diuretics) and vasoconstrictor tone (calcium channel blockers and alpha-adrenoceptor antagonists). Furthermore, it is also recognised that the endothelium is an important contributor in the regulation of the circulation (Cines et a., Blood 1998; 91(10): 3527–3561). It is not surprising, therefore, that endothelial dysfunction has been implicated in the pathogenesis of cardiovascular diseases such as hypertension, atherosclerosis, coronary spastic angina, diabetes and CHF, and further, that endothelial function is now recognized as a therapeutic target for antihypertensive therapies (Ferro and Webb, Drugs 1997; 53 Suppl 1: 30–41). Although certain agents such as ACE inhibitors, and calcium channel blockers are recognised as either protective against, or corrective for, endothelial dysfunction (Naruse et al., J Hypertens 1999; 17(1): 53–60), the relative capacity of different antihypertensive therapies to modify endothelial function has not been fully established. It may be that the beneficial impact of a therapeutic agent on the endothelium is a critical attribute of its clinical efficacy.

Previous findings emphasize the importance of maintaining endothelial function in the regulation of blood pressure, particularly the balance between nitric oxide (NO) and endothelin (ET) (Banting et al., J Hypertens 1996, 14(8): 975–981; Adams et al., Erectile Dysfunction Issues in Current Pharmacology. London: Marin Dunitz, 1998: 11.1–11.12; Adams et al., Int J Impot Res 1996, 8:124; Filep, Hypertension 1997, 30(1 Pt 1): 22–28; Pollock et al., Eur J Pharmacol 1998, 346(1): 43–50; Rees et al., Proc Natl Acad Sci USA 1989, 86(9): 3375–3378; Richard et al., Circulation 1995, 91(3): 771–775). In vivo mechanisms associated with alterations in endothelial function, in particular those linked to these key regulatory factors, have not been elucidated. Previous studies have demonstrated that a deficiency in NO production provokes a marked increase in ET-mediated vasoconstrictor tone, a hallmark of an alteration in vascular function (Banting et al, J Hypertens 1996, 14(8): 975–981; Filep, Hypertension 1997, 30(1 Pt 1): 22–28; Pollock et al., Eur J Pharmacol 1998, 346(1): 43–50; Rees et al., Proc Natl Acad Sci USA 1989, 86(9): 3375–3378; Richard et al., Circulation 1995, 91(3): 771–775).

SUMMARY OF THE INVENTION

According to the invention described in detail hereinbelow, we showed that various depressor and antihypertensive agents negatively influence endothelial function as determined by characterizing endothelin-dependent responses. Specifically, in a conscious rat model we assessed the impact of antihypertensive agents, including alpha-adrenoceptor antagonists, ganglionic blockers, and RAS inhibitors, on responses involving endothelial NO-ET balance.

According to a first aspect, the invention provides a method of preventing or inhibiting adverse cardiovascular effects associated with administration of a sympathetic nervous system antagonist in a subject, comprising administering to a subject in need thereof a sympathetic nervous system antagonist and an endothelin antagonist.

The sympathetic nervous system antagonist and the endothelin antagonist may be administered sequentially, or may be coadministered. The sympathetic nervous system antagonist and the endothelin antagonist may be administered as a single dosage unit.

The sympathetic nervous system antagonist may be an alpha-adrenoceptor antagonist. The alpha-adrenoceptor antagonist may be selected from the group consisting of doxazosin, prazosin, terazosin, and phentolamine.

The sympathetic nervous system antagonist may be a ganglionic blocking agent. The sympathetic nervous system antagonist may be selected from the group consisting of hexamethonium, mecamylamine, clonidine, guanethidine, and reserpine.

The endothelin antagonist may be selected from the group consisting of ABT-627, Bosentan, SB209670, and an NO-mimetic.

According to a second aspect, the invention provides a method of treating hypertension in a subject, comprising administering to a subject in need thereof a sympathetic nervous system antagonist and an endothelin antagonist.

The sympathetic nervous system antagonist and the endothelin antagonist may be administered sequentially, or may be coadministered. The sympathetic nervous system antagonist and the endothelin antagonist may be administered as a single dosage unit.

The sympathetic nervous system antagonist may be an alpha-adrenoceptor antagonist. The alpha-adrenoceptor antagonist may be selected from the group consisting of doxazosin, prazosin, terazosin, and phentolamine.

The sympathetic nervous system antagonist may be a ganglionic blocking agent. The sympathetic nervous system antagonist may be selected from the group consisting of hexamethonium, mecamylamine, clonidine, guanethidine, and reserpine.

The endothelin antagonist may be selected from the group consisting of ABT-627, Bosentan, SB209670, and an NO-mimetic.

According to a third aspect, the invention provides a method for improving the efficacy of a sympathetic nervous system antagonist, comprising administering to a subject in need thereof a sympathetic nervous system antagonist together with an endothelin antagonist.

The sympathetic nervous system antagonist and the endothelin antagonist may be administered sequentially, or may be coadministered. The sympathetic nervous system antagonist and the endothelin antagonist may be administered as a single dosage unit.

The sympathetic nervous system antagonist may be an alpha-adrenoceptor antagonist. The alpha-adrenoceptor antagonist may be selected from the group consisting of doxazosin, prazosin, terazosin, and phentolamine.

The sympathetic nervous system antagonist may be a ganglionic blocking agent. The sympathetic nervous system antagonist may be selected from the group consisting of hexamethonium, mecamylamine, clonidine, guanethidine, and reserpine.

The endothelin antagonist may be selected from the group consisting of ABT-627, Bosentan, SB209670, and an NO-mimetic.

According to a fourth aspect of the invention, the invention provides a method of treating prostate cancer or benign prostate hyperplasia (BPH) in a subject, comprising administering to a subject in need thereof a sympathetic nervous system antagonist and an endothelin antagonist.

The sympathetic nervous system antagonist and the endothelin antagonist may be administered sequentially, or may be coadministered. The sympathetic nervous system antagonist and the endothelin antagonist may be administered as a single dosage unit.

The sympathetic nervous system antagonist may be an alpha-adrenoceptor antagonist. The alpha-adrenoceptor antagonist may be selected from the group consisting of doxazosin, prazosin, terazosin, and phentolamine.

The sympathetic nervous system antagonist may be a ganglionic blocking agent. The sympathetic nervous system antagonist may be selected from the group consisting of hexamethonium, mecamylamine, clonidine, guanethidine, and reserpine.

The endothelin antagonist may be selected from the group consisting of ABT-627, Bosentan, SB209670, and an NO-mimetic.

BRIEF DESCRIPTION OF THE DRAWINGS

Embodiments of the invention will now be described, by way of example, with reference to the accompanying figures, as follows.

DETAILED DESCRIPTION OF THE INVENTION

Figure 1:
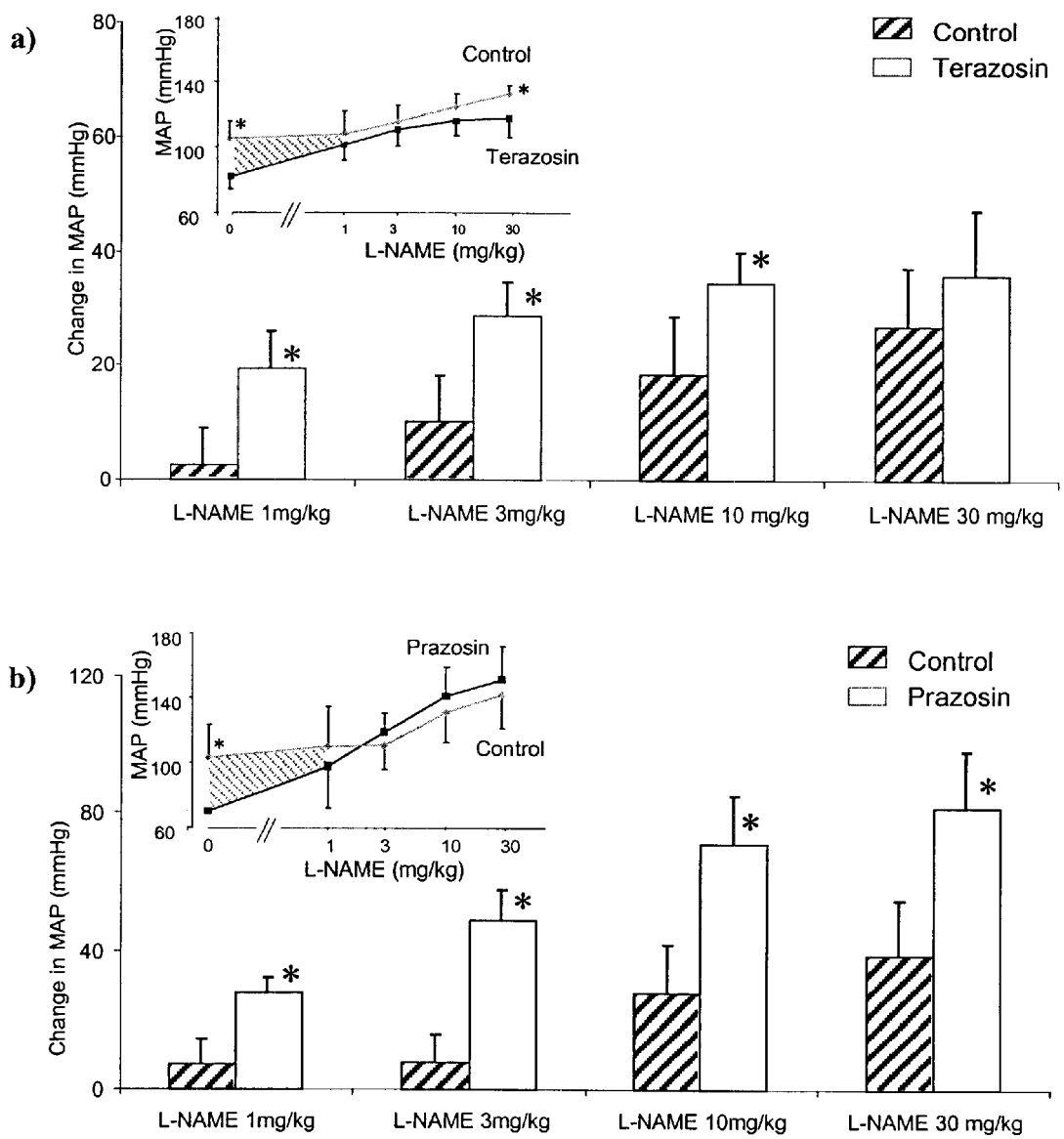
FIG. 1. Pressor response to increasing NOS antagonism (1,3,10,30 mg/kg L-NAME i.v.) was enhanced by pretreatment with a,-adrenoceptor antagonists a) terazosin (2 mg/kg i.v.) or b) prazosin (3 mg/kg i.v.). Data are presented both as change in MAP (mmHg) and absolute MAP (mmHg; inserts). Values represent mean±SD for Trz (n=6 treated, 6 control) and Prz (n=6 treated, 8 control). * indicates significant from control ($p<0.001$).

Use of alpha-adrenergic antagonists such as terazosin and prazosin for the management of hypertension is well known in the art. However, recent evidence from the Antihypertensive and Lipid-Lowering Treatment to Prevent Heart Attack Trial (ALLHAT) (ALLHAT Officers and Coordinators for the ALLHAT Collaborative Research Group, JAMA 283:1967–1975, 2000; the contents of all publications cited in this disclosure are incorporated herein by reference in their entirety) has shown that patients using the alpha-adrenoceptor antagonist doxazosin for the long term management of their hypertension had a statistically significant 25% higher incidence of major cardiovascular disease events such as a doubled risk of congestive heart failure and increased risk of stroke, coronary revascularization, and angina. As a result of this interim analysis it was recommended that the doxazosin treatment arm in the blood pressure component of the trial be discontinued. Furthermore, results of a Veterans Administration Cooperative Study showed that mortality among patients with chronic congestive heart failure was the same for a prazosin-treated group when compared with the placebo group, whereas those given either hydralazine or isosorbide dinitrate was reduced significantly.

Alpha-adrenergic antagonists are also commonly used in the treatment of prostate cancer and benign prostatic hyperplasia (BPH). Recent reports indicate that there is a link between elevated endothelin levels and a negative outcome for prostate cancer or BPH patients (Nelson et al., American Society of Clinical Oncology (ASCO) 2001, No. 12; Singh et al ASCO 2001, No. 1567). The inventors conceive that treatment of prostate cancer or BPH with an alpha-antagonist would upregulate endothelin activity, which, based on these reports, would lead to a poorer clinical outcome. Therefore, according to the present invention, treatment of prostate cancer or BPH with an alpha-adrenoceptor antagonist should be undertaken in combination with an endothelin antagonist.

The present inventors have found that antagonism of the sympathetic nervous system, using either ganglionic blockade or alpha-adrenoceptor antagonism, induces an endothelin-dependent form of endothelial dysfunction which results in a circulatory abnormality. It was found that sympathetic nervous system antagonism by either mechanism markedly enhanced the vasodilatory response to administration of NO mimetics, similar to that induced by nitric oxide synthase antagonism. Also, by combining low doses of a nitric oxide synthase antagonist with a sympathetic nervous system antagonist, the hypersensitivity to NO mimetics was further amplified. It is believed that this hypersensitivity is responsible for the adverse effects of alpha-adrenergic antagonist administration discussed in the above-mentioned ALLHAT study. Specifically, the present inventors believe that sympathetic nervous system antagonists induce an endothelial imbalance in the circulation, and inappropriate cardiovascular responses to this imbalance are responsible for the adverse effects discussed above. This can be overcome in accordance with the instant invention wherein administration of an endothelin antagonist together with an agent that antagonizes the sympathetic nervous system, e.g., a ganglionic blocking agent or an alpha-adrenoceptor antagonist, restores the balance and alleviates and/or prevents the adverse effects of the sympathetic nervous system antagonist.

Figure 3:
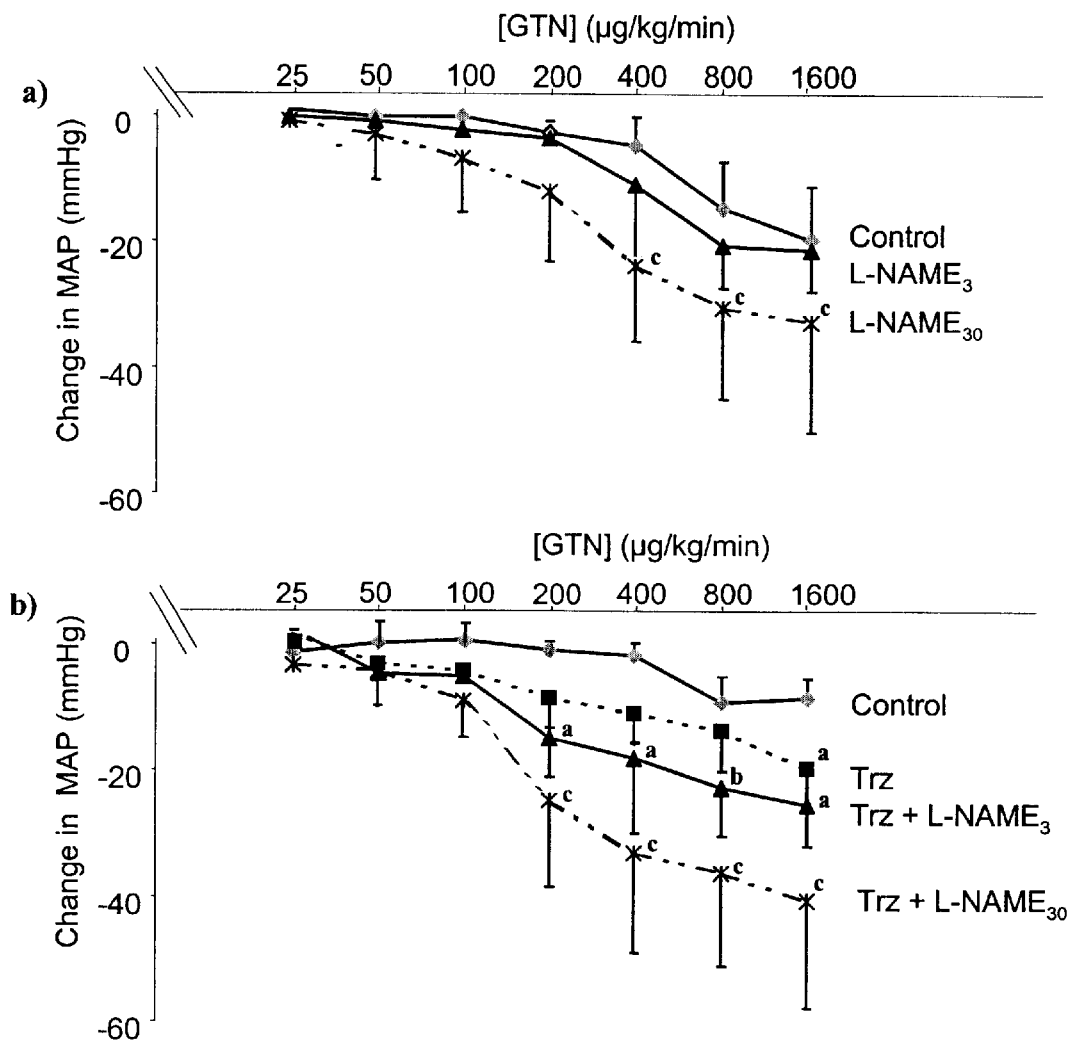
FIG. 3. $\alpha_1$-adrenoceptor antagonism induced hyperresponsiveness to glyceryl trinitrate (25–1600 μg/kg/min GTN i.v.) and enhanced the hyperresponsiveness induced by progressive NOS blockade with low and high dose L-NAME (3 mg/kg and 30 mg/kg, respectively). a) The depressor response to GTN alone and in the presence of low dose and high dose L-NAME (n=6). b) The effect of terazosin (2 mg/kg i.v.) on GTN-mediated depressor responses (n=6). Data are the change in MAP (mmHg) from baseline (mean±SD, n=6). The indicators represent significant differences ($p<0.05$) as follows: a=significant from control, b=from control and terazosin, c=from all other groups.

The present inventors' interpretation of the congestive heart failure (CHF) data in FIG. 3 of the ALLHAT report, which shows Kaplan-Meier estimates for outcomes in the doxazosin and chlorthalidone groups, is that very early during the first year of treatment with the alpha-adrenoceptor antagonist doxazosin, patients rapidly increase their risk of developing CHF. In fact, the line for the doxazosin-treated group has its steepest slope during the first six months of treatment indicating the highest increase in risk for developing CHF when compared to the chlorthalidone-treated group. Beyond this early stage, one might argue that there is a much more modest increase in the slope for the doxazosin-treated group compared with the chlorthalidone-treated group indicating a slight increase in risk for developing CHF. This novel interpretation of the data indicates that patients given alpha-adrenoceptor antagonists to treat their hypertension are potentially at a 10 to 20-fold greater risk for developing CHF early during treatment, a characteristic of alpha-adrenoceptor antagonists which is very different from the other treatments such as chlorthalidone. Administration of an endothelin antagonist together with an alpha-adrenoceptor antagonist in accordance with the present invention can substantially reduce this risk.

According to a broad aspect, this invention relates to use of an endothelin antagonist for treating a sympathetic nervous system imbalance associated with administration of a sympathetic nervous system antagonist. In accordance with the invention, the endothelin antagonist can be administered substantially simultaneously with the sympathetic nervous system antagonist (i.e., coadministered), or the two agents can be administered sequentially according to a suitable schedule readily determined by one of ordinary skill in the art.

According to another aspect of the invention there is provided a pharmaceutical composition comprising, in combination, an endothelin antagonist and a sympathetic nervous system antagonist, as a single dosage unit. The single dosage unit can further comprise any pharmaceutically acceptable vehicle. The single dosage unit provides for simultaneous or substantially simultaneously administration of the endothelin antagonist and a sympathetic nervous system antagonist.

As used herein, the term "treating" is intended to mean inhibiting, reducing, preventing (e.g., prophylaxis), reversing (e.g., alleviating), ameliorating, controlling, or managing.

As used herein, the term "sympathetic nervous system antagonist" is intended to mean any agent which effectively inhibits, either directly or indirectly, the actions of the sympathetic nervous system. In a preferred embodiment, the actions of the sympathetic nervous system on alpha adrenoceptors are inhibited. Thus, sympathetic nervous system antagonists according to the invention encompass alpha-adrenoceptor antagonists, including $\alpha_1$ and $\alpha_2$ antagonists, as well as ganglionic blocking agents. Examples of alpha-adrenoceptor antagonists include, but are but not limited to, doxazosin, prazosin, terazosin, and phentolamine. Examples of other sympathetic nervous system antagonists include the ganglionic blocking agents hexamethonium and mecamylamine, as well as clonidine, guanethidine, and reserpine. Sympathetic nervous system antagonists are used, for example, as anti-hypertensive agents. Further exemplary agents are listed in Table 1.

As used herein, the term "adverse cardiovascular effect" is intended to encompass any adverse effect exhibited by a subject to whom a sympathetic nervous system antagonist has been administered. An adverse cardiovascular effect can be, for example, hypertension, congestive heart failure, stroke, coronary revascularization, peripheral artery disease, fatal and non-fatal myocardial infarction, vasospasm, thrombotic events, syncope, endothelial dysfunction, atherosclerosis, angina, systemic pathogenic vascular remodeling, and cancer, tumor angiogenesis, and metastasis, sexual dysfunction, or an increase in the subject's probability of acquiring any such disease.

As used herein, the term "endothelin antagonist" is intended to mean any pharmaceutically acceptable compound which effectively inhibits, prevents or blocks the actions of endothelin, either directly or indirectly, including any pharmaceutically acceptable salt, ester, or prodrug thereof. For example, an endothelin antagonist according to the invention may act at the level of inhibiting endothelin-receptor binding, inhibiting endothelin converting enzyme, inhibiting release of endothelin from endothelial cells or inhibiting post-receptor intracellular signal transduction pathways. Both peptidic and non-peptidic compounds are encompassed by this term. Numerous endothelin antagonists, such as endothelin receptor A ($ET_A$) and endothelin receptor B ($ET_B$) antagonists, and pharmaceutically acceptable salts thereof, have been identified and can be obtained commercially (e.g., Sigma, American Peptide Company Inc.). Attention is also directed to U.S. Pat. No. 5,284,828 issued Feb. 8, 1994 to Hemmi et al., U.S. Pat. No. 5,378,715 issued Jan. 3, 1995 to Stein et al., and U.S. Pat. No. 5,382,569 issued Jan. 17, 1995 to Cody et al., which describe in detail the chemical structures of various endothelin receptor antagonists, and to U.S. Pat. No. 5,338,726 issued Aug. 16, 1994 to Shinosaki et al., which describes the chemical structure of endothelin converting enzyme inhibitors. Table 2 shows exemplary endothelin antagonists, including those employed in the working examples set forth below.

For example, $ET_A$ and $ET_B$ antagonists are available commercially from various sources such as American Peptide Company Inc. and include:

| NAME | FORMULA | CAT NO. |
|---|---|---|
| $ET_A$ | | |
| Endothelin Antagonist | c(DTrp-DAsp-Pro-DVal-Leu) | 88-2-10 |
| Endothelin Receptor Antagonist (BE18257B) | c(DGlU-Ala-Allo-DIle-Leu-DTrp) | 88-2-20 |
| Endothelin Antagonist (JKC-301) | c(DIle-Leu-DTrp-DAsp-Pro) | 88-2-30 |
| Endothelin Antagonist (JKC-302) | c(DVal-Leu-DTrp-DSer-Pro) | 88-2-31 |
| Endothelin Antagonist (BQ-610) | (N,N-hexamethylene)carbamoyl-Leu-DTrp(CHO)-DTrp | 88-2-32 |
| Endothelin Antagonist (W-7338A) | c(DGlu-Ala-DVal-Leu-DTrp) | 88-2-40 |
| $ET_B$ | | |
| [Cys11, Cys 15]Endothelin-1 (8-21), (IRL-1038) | c(DGlu-Ala-DVal-Leu-DTrp) | 88-2-41 |
| [Ala11, 15]Endothelin-1 (6-21), N-Acetyl | Ac-Leu-Met-Asp-Lys-Glu-Ala-Tyr-Phe-Ala-His-Leu-Asp-Ile-Ile-Trp | 88-2-42 |
| N-Suc-[Glu9, Ala11 ,15]Endothelin-1, (8-21), (LRL-1620) | Suc-Asp-Glu-Glu-Ala-Val-Tyr-Phe-Ala-His-Leu-Asp-Ile-Ile-Trp | 88-2-50 |

A preferred endothelin antagonist according to the invention is an endothelin receptor A antagonist (ETRA).

An NO-mimetic can be an endothelin antagonist, since NO-mimetics can regulate the actions of endothelin on the circulation. As used herein, the term "NO-mimetic" is intended to mean any compound which mimics the effects of NO, generates or releases NO through biotransformation, any compound which generates NO spontaneously, any compound which spontaneously releases NO, or any compound which in any other manner generates NO or an NO-like moiety when administered to a mammal. Such a compound can also be referred to as a "NO donor", "NO prodrug", "NO producing agent", "NO delivering compound", "NO generating agent" and "NO provider". Examples of such compounds include, but are not necessarily limited to: so-called "organonitrates" such as nitroglycerin (GTN), isosorbide 5-mononitrate (ISMN), isosorbide dinitrate (ISDN), pentaerythritol tetranitrate (PETN), erythrityl tetranitrate (ETN), amino acid derivatives such as N-hydroxy-L-arginine (NOHA), $N^6$-(1-iminoethyl)lysine) (L-NIL), L-$N^5$-(1-iminoethyl)ornithine (LN-NIO), $N^y$-methyl-L-arginine (L-NMMA), and S-nitrosoglutathione (SNOG); other compounds which generate or release NO under physiological conditions such as S,S-dinitrosodithiol (SSDD), [N-[2-(nitroxyethyl)]-3-pyridinecarboxamide (nicorandil), sodium nitroprusside (SNP), S-nitroso-N-acetylpenicillamine (SNAP), 3-morpholino-sydnonimine (SIN-1), molsidomine, DEA-NONOate (2-(N,N-diethylamino)-diazenolate-2-oxide), spermine NONOate (N-[4-[1-(3-aminopropyl)-2-hydroxy-2-nitrosohydrazino] butyl-1,3-propanediamine), and NO gas, or a functional equivalent thereof. The organic nitrates GTN, ISMN, ISDN, ETN, and PETN, as well as nicorandil are commercially available in pharmaceutical dosage forms (see Tables 3 and 4). SIN-1, SNAP, S-thioglutathione, L-NMMA, L-NIL, L-NIO, spermine NONOate, and DEA-NONOate are commercially available from Biotium, Inc. 183 Shoreline Court, Richmond, Calif., USA.

that has NO-like activity, or that mimics the effect of NO. Such compounds do not necessarily release, generate or provide NO, but produce the same effect as NO on a pathway that is affected by NO. NO can have both cyclic GMP-dependent and cyclic GMP-independent effects. NO is known to activate the soluble form of guanylyl cyclase thereby increasing intracellular levels of the second messenger cyclic GMP. Accordingly, compounds which directly activate guanylyl cyclase, such as, for example, 3-(5'-hydroxymethyl-2'furyl)-1-benzyl indazole (YC-1), or which act as cyclic-GMP analogues, such as, for example, 8-bromo-cyclic-GMP (8-Br-cGMP) and 8-(4-chlorophenylthio)guanosine 3', 5'-cyclic monophosphate (8-PCPT-cGMP), would also be considered to be NO-mimetics. Also encompassed are the natriuretic peptide family, including atrial natriuretic peptide (ANP), brain natriuretic peptide (BNP), C-type natriuretic peptide (CNP), and Urodilatin (URO); these peptides have tissue-specific distribution as follows: heart, ANP, BNP; brain, ANP, BNP,

TABLE 1

| Brand/Trade Name | Manufacturer | Active Drug Name | Recommended Dose for Treatment of Hypertension | Recommended Dose for Treatment of Benign Prostatic Hypertension | Commercially Available Preparations | Preferred dose according to the present invention |
|---|---|---|---|---|---|---|
| CARDURA-1 ™ ⓑ CARDURA-2 ™ ⓑ CARDURA-4 ™ ⓑ | AstraZeneca | Doxazosin Mesylate | 1–16 mg once daily | 1–8 mg once daily | 1, 2, 4 mg tablets | 0.1–8 mg once daily |
| MINIPRESS ™ ⓑ | Pfizer | Prazosin HCl | 0.5 b.i.d. or t.i.d., up to 15 mg per day | 0.5 b.i.d. or t.i.d., up to 15 mg per day | 1, 2, 5 mg tablets | 0.05 b.i.d. or t.i.d., up to 8 mg per day |
| ALTI-PRAZOSIN ⓑ | AltiMed (generic) | Prazosin HCl | 0.5 b.i.d. or t.i.d., up to 15 mg per day | 0.5 b.i.d. or t.i.d., up to 15 mg per day | 1, 2, 5 mg tablets | 0.05 b.i.d. or t.i.d., up to 8 mg per day |
| APO ®-PRAZO ⓑ | Apotex (generic) | Prazosin HCl | 0.5 b.i.d. or t.i.d., up to 15 mg per day | 0.5 b.i.d. or t.i.d., up to 15 mg per day | 1, 2, 5 mg tablets | 0.05 b.i.d. or t.i.d., up to 8 mg per day |
| NOVO-PRAZIN ⓑ | Novopharm (generic) | Prazosin HCl | 0.5 b.i.d. or t.i.d., up to 15 mg per day | 0.5 b.i.d. or t.i.d., up to 15 mg per day | 1, 2, 5 mg tablets | 0.05 b.i.d. or t.i.d., up to 8 mg per day |
| NU-PRAZO ⓑ | Nu-Pharm (generic) | Prazosin HCl | 0.5 b.i.d. or t.i.d., up to 15 mg per day | 0.5 b.i.d. or t.i.d., up to 15 mg per day | 1, 2, 5 mg tablets | 0.05 b.i.d. or t.i.d., up to 8 mg per day |
| HYTRIN ® ⓑ | Abbott | Terazosin HCl Dihydrate | 1–20 mg per day | 1–10 mg once daily | 1, 2, 5, 10 mg tablets | 0.1–10 mg per day |
| ALTI-TERAZOSIN ⓑ | AltiMed (generic) | Terazosin HCl | " | " | 1, 2, 5, 10 mg tablets | " |
| APO ®-TERAZOSIN ⓑ | Apotex (generic) | Terazosin HCl | " | " | 1, 2, 5, 10 mg tablets | " |
| NOVO-TERAZOSIN ⓑ | Novopharm (generic) | Terazosin HCl | " | " | 1, 2, 5, 10 mg tablets | " |
| NU-TERAZOSIN ⓑ | Nu-Pharm (generic) | Terazosin HCl | " | " | 1, 2, 5, 10 mg tablets | " |

*information for this table was obtained from the USP DI ® Drug Guide and the Compendium of Pharmaceuticals and Specialties Thirty-fifth Edition 2000

TABLE 2

| Endothelin Receptor Antagonist | Doses in Humans for various disease states |
|---|---|
| ABT-627 | 2.5–70 mg per day |
| Bosentan | 1–2 g per day (CHF) |
| SB209670 | 1–3 mg/kg i.v. *** (in dogs) |

As used herein, the term "NO-mimetic" is also intended to mean any compound that acts as a NO pathway mimetic, CNP; endothelial cells, CNP; and kidney, URO. The selectivity of a NO-mimetic acting as an endothelin antagonist can be enhanced by using the NO-mimetic at low doses. By "low doses" is meant doses which do not appreciably alter systemic circulation or vascular tone.

Insofar as the ALLHAT study discussed above found that alpha-adrenoceptor antagonists such as doxazosin, administered as an anti-hypertensive agent, are associated with increased risk for cardiovascular disease, the invention provides a treatment for hypertension in which such risk is reduced. In accordance with this aspect of the invention there is provided a method for treating hypertension in a subject comprising administering to the subject a sympathetic nervous system antagonist and an endothelin antagonist.

In accordance with yet another aspect of this invention there is provided a method for improving the efficacy of a sympathetic nervous system antagonist, comprising administering a sympathetic nervous system antagonist together with an endothelin antagonist.

Examples of sympathetic nervous system antagonists suitable for use in accordance with the present invention are shown in Table 1. Dosages of these exemplary agents can be as high as those recommended by the manufactures (see column 4 of Table 1); however, the invention contemplates dosages as low as one-tenth of those recommended dosages, and up to one-fourth to one-half of those recommended dosages. For example, for Cardura™, the dosage in accordance with the invention is about 0.1 mg to about 16 mg once daily, about 0.1 mg to about 8 mg once daily, or about 0.1 mg to about 4 mg twice daily. Dosage ranges for the remaining exemplary agents in Table 1 can similarly be determined.

In addition to the agents listed above, further examples of endothelin antagonists suitable for use in accordance with the present invention include ABT-627 (Abbott, Ill.), Bosentan (Ro 47-0203; Roche, N.J.) and SB209670 (SmithKline Beecham, Pa.), and GTN listed in Table 2. The dosages for each of these agents in Table 2 are exemplary; however the invention contemplates smaller dosages.

Pharmaceutical Formulations

Pharmaceutical formulations for the administration of an endothelin antagonist in combination with a sympathetic nervous system antagonist in accordance with the method of the present invention may take the form of ointments, transdermal patches, transbuccal patches, injectables, nasal inhalant forms, spray forms for deep lung delivery through the mouth, orally administered ingestable tablets and capsules, and tablets or lozenges, or "lollipop" formulations for administration through the oral mucosal tissue. The latter formulations included tablets, lozenges and the like which are dissolved while being held on or under the tongue, or in the buccal pouch.

The pharmaceutical compositions of the present invention comprise a therapeutically effective amount of an endothelin antagonist in combination with a sympathetic nervous system antagonist formulated together with one or more pharmaceutically acceptable carriers. As used wherein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), supralingually (on the tongue) sublingually (under the tongue), buccally (held in the buccal pouch), or as an oral or nasal spray. The oral spray may be in the form of a powder or mist which is delivered to the deep lungs by oral inhalation.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In cases where it is desirable to prolong the effect of the drug, the absorption of the drug from subcutaneous or intramuscular injection can be slowed. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like. The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention. Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

A preferred mode of delivery is one which provides a reasonably steady-state delivery of therapeutic agents, so as to maintain steady-state plasma concentrations. Such delivery avoids any substantial initial spike in plasma concentration of the agent, as it would be desirable to avoid any spike supra-threshold for negative side effects. Solid dosage forms, including sustained-release solid dosage foms, for oral administration include capsules, tablets, pills, powders, and granules, and are a preferred mode of delivery.

EXAMPLES

Example 1

General Methods

Animals: Male Sprague-Dawley rats (250–300 g) from Charles River Laboratories (St. Constant, Quebec) were individually housed under conditions of 12-hour light/dark cycle at a room temperature of 22–24° C. Purina® rodent chow and tap water were provided ad libitum. Rats were housed for at least one day prior to catheter implantation and allowed a minimum of 3 days to recover from the surgery before any experiments. This post-surgery recovery period was previously determined as the time required for return of normal vascular response to vasoactive agents (unpublished data). Experiments were performed in accordance with standards established by the Canadian Council of Animal Care.

Surgery: The surgical technique was based on that described by Thompson et al. (Hypertension. 20(6):809–815, 1992). In brief, rats were anaesthetized with Hypnorm®/Nersed® (1:2:1 ratio of Hypnorm®:H$_2$O:Versed® at a dose rate of 3 ml/kg i.p.). Catheters made of small bore Teflon® tubing (0.012-inch i.d., 30 gauge, Cole-Parmer, Laval, Quebec) inserted into vinyl tubing (0.02-inch i.d., 23 gauge) were implanted into the abdominal aorta (x1) and the inferior vena cava (x2) distal to the kidneys and secured in place with cyanoacrylate glue. An additional catheter sat loosely in the abdominal cavity for intra-peritoneal administration of drugs. All catheters were tunneled subcutaneously, exteriorized at the nape of the neck and sutured into place. The catheters were filled with heparin saline (50 IU/ml) and sealed at the exposed end.

Determination of MAP: Three days after surgery, MAP was recorded (PowerLab/8s DAS, ADInstruments, Milford, Mass.). The aortic catheter was connected via vinyl tubing to a pressure transducer (BP-100, CB Sciences, Dover, N.H.). The electrical signal was amplified (ETH-400 Transducer Amplifier, CB Sciences, Dover, N.H.) and converted to a pulsatile waveform using PowerLab/8s hardware equipped with Chart version 3.6/s. An equilibration period of at least 1 hour was allowed prior to any experimentation to establish a steady baseline. Drugs were administered either using intravenous catheters for bolus injections and constant infusions or an intra-peritoneal catheter for bolus doses as specified. Mean arterial pressure (MAP) and heart rate (HR) were calculated as an average over five minutes for steady state conditions and 10 seconds for transient drug responses.

Data Analysis: Dose responses to $N^\omega$-nitro-L-arginine-methyl ester (L-NAME, Sigma, Mo.) in terazosin- or prazosin-treated animals vs control were compared using unpaired, two-tailed t-test for each dose. Comparison of dose responses to NO-mimetics between treatments was initially analyzed with a repeated measures two-way ANOVA. To further identify significance at each dose a one-way ANOVA followed by a Newman-Keuls Post Hoc test was used. In example 4, the data was analyzed using a repeated measures two-way ANOVA (analysis of variance) to analyze treatment effects and two-tailed independent t-tests were used to compare individual doses between groups. In all cases a p value less than 0.05 was considered to be statistically significant.

Example 2

Impact of Removing of $\alpha_1$-adrenoceptor Signaling on Regulation of the Circulation The impact of neural control on changes in MAP induced by NOS blockade was investigated to determine what role, if any, α-adrenoceptor mediated vasoconstriction played in the pressor response. The NOS antagonist L-NAME was administered in increasing doses (1,3,10,30 mg/kg i.v.). MAP was measured after each dose when pressure reached steady state (10 min). To assess the influence of adrenergic signaling during vasoconstriction, $\alpha_1$-adrenoceptors were maximally blocked by pre-treatment of the animals with one of two $\alpha_1$-adrenoceptor antagonists, terazosin (2 mg/kg i.v.) or prazosin (3 mg/kg i.v.) (doses were previously determined to be maximal, i.e., further increases in dose did not result in further lowering of MAP) and twenty minutes were allowed for pressure to reach steady state before the L-NAME was administered. Dose responses to the NOS antagonist were then completed as previously described.

Administration of alpha-adrenoceptor antagonists lowered MAP significantly in both prazosin- or terazosin-treated animals (prz: ↓36.35±13.96 mmHg, trz: ↓128.09±18.49 mmHg). FIG. 1 (insert) shows the steady state pressure after $\alpha_1$-adrenoceptor antagonism compared with control. A single dose of 1 mg/kg L-NAME was sufficient to normalize the MAP in terazosin- or prazosin-treated rats compared to controls. This was because of a significantly enhanced response in the treated animals to NOS antagonism (FIG. 1). The change in pressure with each cumulative dose of L-NAME is larger in animals pre-treated with an $\alpha_1$-adrenoceptor antagonist. At maximal NOS blockade, the pressor response in the presence of complete alpha-adrenoceptor antagonism was blunted in the terazosin-treated animals, but not in the prazosin-treated animals.

Example 3

The Impact of Removing $\alpha_1$-adrenoceptor on Vascular Reactivity to NO-mimetics Initial experiments assessing the role of alpha-adrenoceptors in NO-deficient hypertension indicated that alpha-adrenoceptor antagonism had the ability to modify the vascular response to low doses L-NAME (3 mg/kg i.v.). NOS blockade hypertension also results in a hypersensitivity to NO-mimetics such as SNP and GTN. This set of experiments examined whether alpha-adrenoceptor antagonism and/or complete removal of α-signaling could also alter vascular reactivity to exogenous NO. Dose response curves to 30 second infusions of the NO-mimetics sodium nitroprusside (1–30 μg/kg/min SNP i.v.) or glyceryl trinitrate (25–1600 μg/kg/min GTN i.v.) were generated in control animals to determine normal vasodilatory reactivity to exogenous NO. Reactivity was then determined following minimal and maximal NOS blockade by administration of a low dose followed by a high dose of L-NAME (3 and 30 mg/kg L-NAME i.v., respectively). To characterize the impact of the removal of $\alpha_1$-adrenoceptor signaling on the vascular response to NO-mimetics, a sub-group of animals were pre-treated with terazosin (2 mg/kg i.v.) to induce maximal blockade of the $\alpha_1$-adrenoceptors before L-NAME administration. In these animals additional dose responses to each NO-donor were performed after initial alpha-adrenoceptor antagonism and before L-NAME treatment. Further assessment of the impact of removal of $\alpha_1$-adrenoceptor signaling was made through ganglionic blockade with hexamethonium (30 mg/kg i.v.). Down-stream sympathetic signaling is effectively abolished by completely blocking the ganglia with hexamethonium. After establishment of a control dose response to SNP, maximal ganglionic blockade was induced and MAP was allowed to reach a steady state. The vascular reactivity to SNP was reassessed after hexamethonium alone and following both a low then high dose of L-NAME (3 and 30 mg/kg L-NAME i.v., respectively).

In one group of animals, (FIG. 2a) the response to the NO-mimetic SNP was enhanced by maximal NOS inhibition (30 mg/kg L-NAME), but not moderate NOS antagonism (3 mg/kg L-NAME). In a second group of animals (FIG. 2b), the depressor response to SNP was enhanced after maximal $\alpha_1$-adrenoceptor blockade. Furthermore, in the terazosin-treated animals, the dose response to SNP in the presence of L-NAME was enhanced relative to control both after maximal NOS blockade (30 mg/kg L-NAME) as well as after only moderate NOS antagonism (3 mg/kg L-NAME). As a control to account for changes in vascular reactivity over time, a second dose response to SNP was performed in animals not receiving terazosin in order to coincide with the second dose response to SNP in animals treated with terazosin. There was no significant difference from control (data not shown).

FIG. 3b shows a similar enhanced depressor response to another NO-mimetic, GTN, following a-adrenoceptor blockade. Although the terazosin treatment alone showed an enhanced GTN-mediated decrease in MAP consistent with the trend observed for SNP (FIG. 2b), it was only statistically significant at the highest dose of GTN. Combined with moderate NOS blockade (3 mg/kg L-NAME), terazosin-treated animals had a significantly enhanced depressor response to GTN. FIG. 3a shows that moderate NOS blockade (3 mg/kg L-NAME) alone did not produce a significant change in vascular reactivity to GTN in control animals. However, maximal NOS blockade (30 mg/kg L-NAME) enhanced the GTN-mediated depressor response in both control (FIG. 3a) and terazosin-treated (FIG. 3b) animals.

Figure 2:
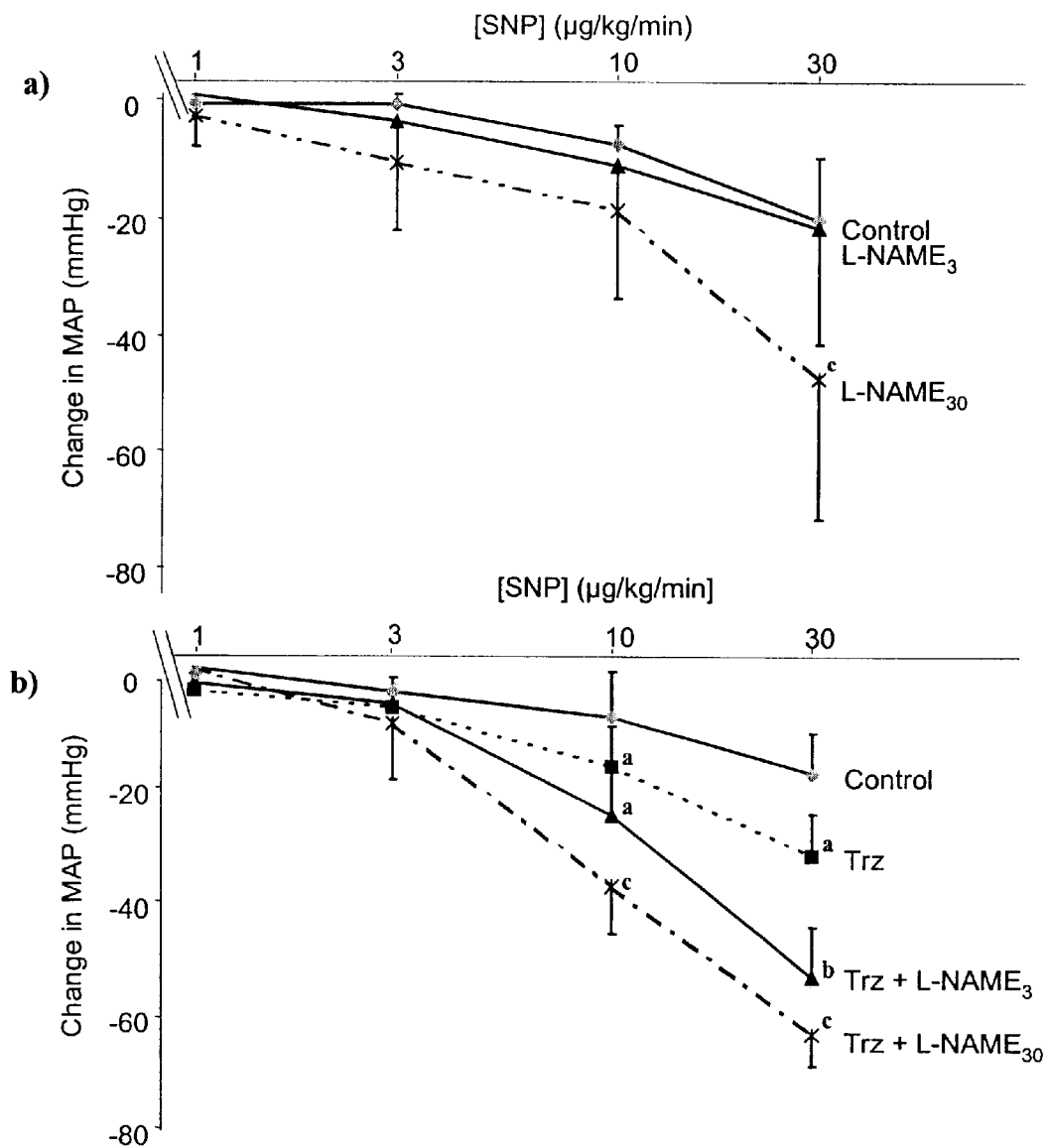
FIG. 2. $\alpha_1$-adrenoceptor antagonism induced hyperresponsiveness to the sodium nitroprusside (1–30 μg/kg/min SNP i.v.) and enhanced the hyperresponsiveness induced by progressive NOS blockade with low and high dose L-NAME (3 mg/kg and 30 mg/kg, respectively). a) The depressor response to SNP alone and in the presence low dose and high dose L-NAME (n=6). b) The effect of terazosin (2 mg/kg i.v.) on depressor responses (n=6). Data are the change in MAP (mmHg) from baseline (mean±SD, n=6). The indicators represent significant differences ($p<0.05$) as follows: a=significant from control, b=from control and terazosin, c=from all other groups.
Figure 4:
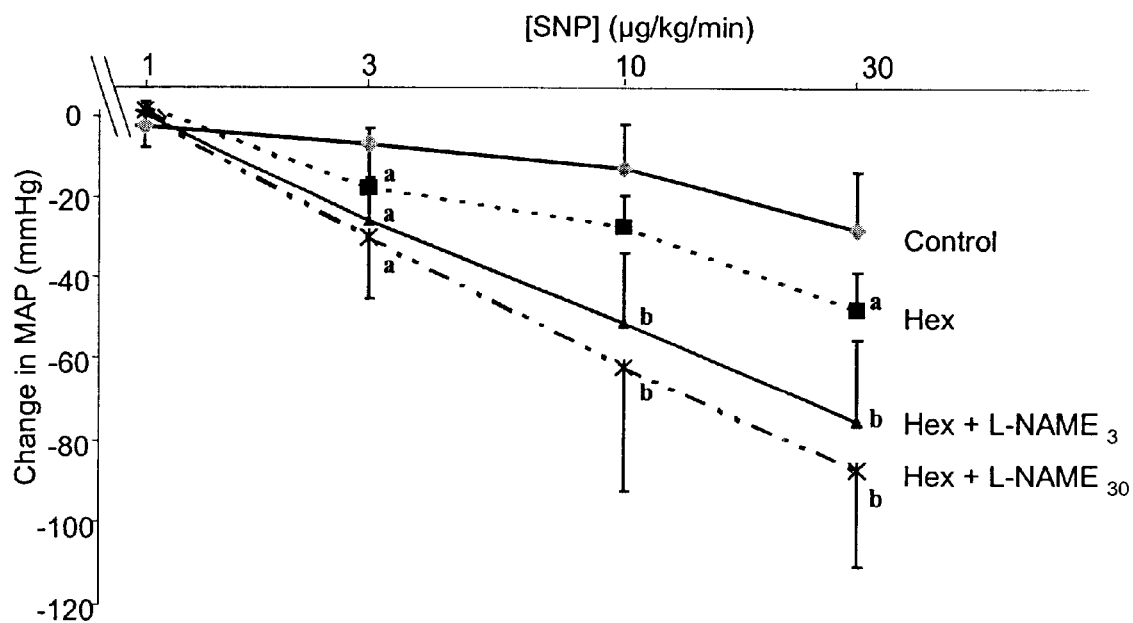
FIG. 4. Ganglionic blockade with hexamethonium (40 mg/kg Hex) induces hyperresponsiveness to the sodium nitroprusside (1–30 μg/kg/min SNP i.v.) and enhances the hyperresponsiveness induced by progressive NOS blockade with low and high dose L-NAME (3 mg/kg and 30 mg/kg, respectively). Data are the change in MAP (mmHg) from baseline (mean±SD, n=6). The indicators represent significant differences ($p<0.05$) as follows: a=significant from control, b=from control and hexamethonium, c=from all other groups.

FIG. 4 demonstrates that removal of α-adrenoceptor signaling by an alternate means, ganglionic blockade with hexamethonium, induced an almost identical pattern of hypersensitivity to SNP-mediated vasodilation when compared to the effects of terazosin on SNP sensitivity (FIG. 2b).

Similarly, both moderate and maximal NOS blockade (3 and 30 mg/kg L-NAME, respectively) combined with hexamethonium treatment, further enhanced the SNP-mediated depressor response (compare FIG. 2b and FIG. 4).

Example 4

Impact of RAS Inhibition on Vascular Reactivity to NO-mimetics

To address the possibility that changes in vascular response to NO-mimetics may be the result of changes in pressure, MAP was lowered by inhibiting the renin-angiotensin system (RAS) with either the combination of an angiotensin converting enzyme (ACE) inhibitor (enalaprilat 30 mg/kg i.p.) together with an angiotensin II type 1 ($AT_1$) receptor antagonist (losartan 30 mg/kg i.p.) in a 1:1 ratio or an $AT_1$ receptor antagonist alone (30 mg/kg i.v.). Dose response curves to SNP were generated before RAS inhibition, after RAS inhibition and after both RAS inhibition and maximal NOS blockade with L-NAME (100 mg/kg i.p.).

Figure 5:
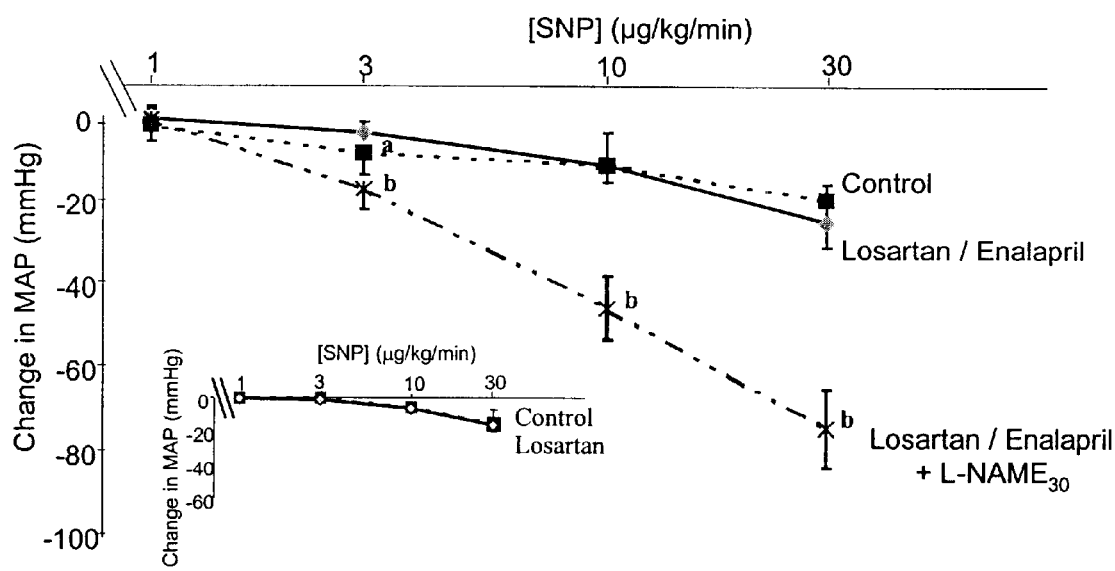
FIG. 5. The depressor response to SNP (1–30 μg/kg, i.v.) was unaltered by combination angiotensin converting enzyme (ACE) inhibition and angiotensin II (Ang II) receptor blockade (1:1 ratio of 30 mg/kg losartan:enalaprilat i.p.) or Ang II blockade alone (30 mg/kg losartan i.v.; insert). Maximal NOS blockade (30 mg/kg L-NAME i.v.) caused hypersensitivity to the SNP depressor response. Data are change in MAP (mmHg) from baseline (mean±SD, n=6, n=5 for insert)). The indicators represent significant differences ($p<0.05$) as follows: a=significant from control, b=from control and terazosin, c=from all other groups.

RAS inhibition with the combined administration of losartan and enalapril caused a decrease in MAP greater than that observed with terazosin alone (37.59±4.60 vs 28.09±18.49). FIG. 5 shows that despite a larger depressor signal from losartan and enalapril compared to terazosin, RAS inhibition does not produce an enhanced depressor response to SNP like that observed after a-adrenoceptor blockade (FIG. 2b) or ganglionic blockade (FIG. 4). Furthermore, RAS inhibition did not alter the hypersensitivity to SNP measured following maximal NOS antagonism (100 mg/kg i.p.). FIG. 5 (insert) also shows that losartan treatment alone failed to increase the sensitivity to the SNP-mediated depressor response.

Example 5

Endothelin Dependency of NO-mimetic Effects

Since the hypersensitivity to NO-mimetics such as SNP and GTN have previously been demonstrated to be endothelin (ET)-dependent, the experiments detailed above assessing changes in the vasodepressor sensitivity to SNP following terazosin and then L-NAME administration were repeated in the presence of an $ET_{A/B}$ receptor antagonist (ETRA), specifically SB209670. An initial dose response to the NO-mimetic SNP (1–30 μg/kg/min) defined the normal vascular reactivity to exogenous NO. The ETRA SB209670 was given as a 50 mg/kg i.v. bolus over 10 minutes followed by a constant infusion of 100 μg/kg/min after an initial SNP dose response assessment. Additional SNP dose response assessments were made at 30 minutes and 60 minutes after the end of the ETRA bolus, after terazosin (2 mg/kg i.v.) administration and finally after L-NAME (3 mg/kg i.v.) administration.

Figure 6:
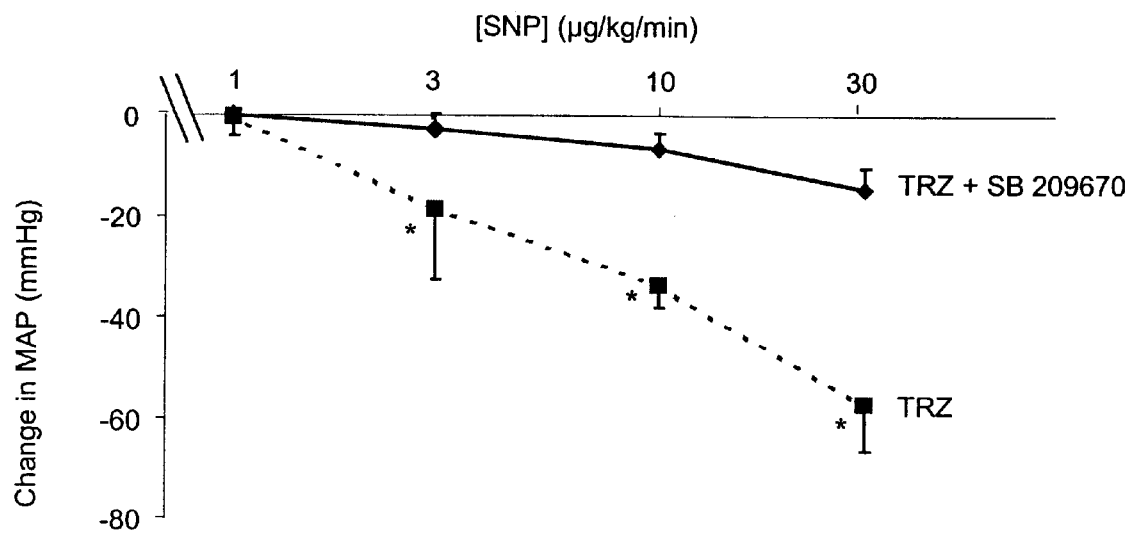
FIG. 6. Concurrent treatment with terazosin and an endothelin antagonist (SB209670 8 mg/kg bolus followed by a 100 µg/kg/min continuous i.v. infusion) significantly prevented the hypersensitivity to the depressor response to the NO-mimetic sodium nitroprusside (1–30 µg/kg/min SNP i.v.) observed when terazosin (2 mg/kg trz i.v.) was administered alone. Data are the change in MAP (mmHg) from baseline (mean±SD, n=6). * indicates that the means were significantly different in a two-tailed independent t-test ($p<0.05$).
Figure 7:
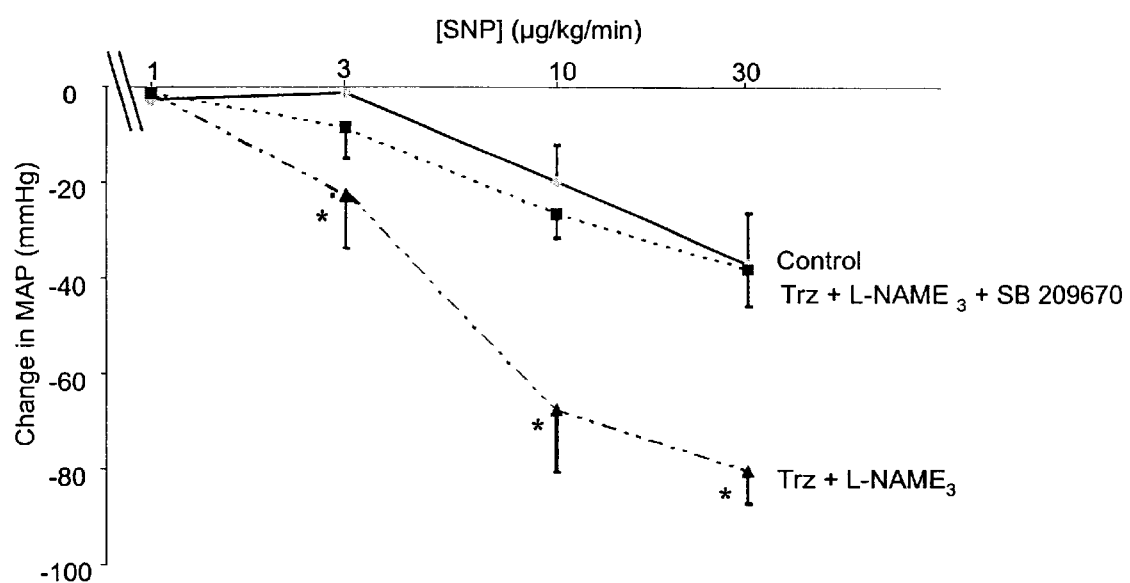
FIG. 7. Concurrent treatment with terazosin, L-NAME and an endothelin antagonist (SB209670 8 mg/kg bolus followed by a 100 µg/kg/min continuous i.v. infusion) prevented the hypersensitivity to the depressor response to the NO-mimetic sodium nitroprusside (1–30 µg/kg SNP i.v.) observed when both terazosin (2 mg/kg i.v.) and a low dose of a NOS antagonist (3 mg/kg L-NAME i.v.) were administered together. Data are the change in MAP (mmHg) from baseline (mean±SD, n=6). * indicates that the means were significantly different in a two-tailed independent t-test ($p<0.05$).

The endothelin antagonist, SB209670, (90.41±4.36 mmHg) did not lower MAP significantly from control (98.29±6.43 mmHg). However, after terazosin treatment MAP was significantly lower in SB209670 treated animals (51.83±4.02 vs 77.37±17.48 mmHg). Terazosin treatment enhanced the dose response to SNP in animals not receiving SB209670, but significantly blunted the dose response in those receiving the endothelin antagonist (FIG. 6). To ensure that the dose response was not blunted due to the inability of MAP to drop lower in an already depressed circulation (i.e., to ensure that blood pressure had not been maximally lowered), a higher bolus dose of SNP was administered to ensure MAP could still drop lower (data not shown). Animal began with SNP dose response curves that were not significantly different. In addition, as seen in FIG. 7, SB209670 prevented the enhanced SNP response that was shown with terazosin combined with moderate NOS antagonism (L-NAME: 3 mg/kg).

Example 6

Combined Analysis of Examples 2, 3 & 4—
Assessment of Homeostatic Mechanisms

Figure 8:
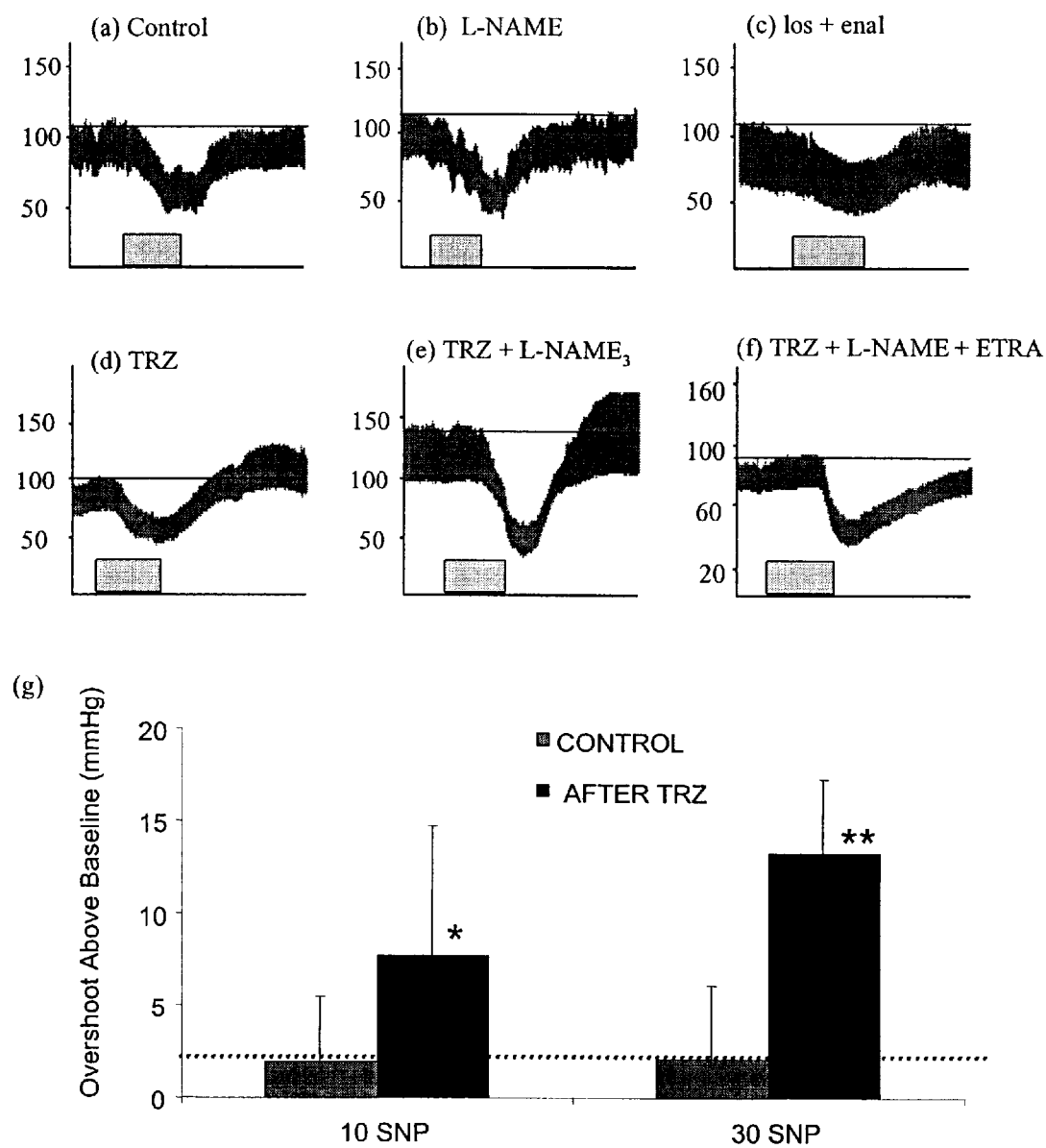
FIG. 8. Representative arterial pressure tracings demonstrating recovery from a 30 second infusion of SNP (shaded area on the trace) in the presence of (a) vehicle, (b) L-NAME, (c) Losartan+Enalaprilat (los+enal), (d) TRZ, (e)TRZ+L-NAME, and (f) TRZ+L-NAME+SB209670. Recovery from the depressor challenge was similar to control in both L-NAME and Losartan/Enalaprilat treated groups. In contrast, there was a marked "overshoot" of the baseline MAP both in TRZ and TRZ+L-NAME treated groups. This effect was abolished by concomitant treatment with an ETRA (see Table 1). (g) After TRZ treatment there is a significant and dose-dependent "overshoot" of the original baseline after a depressor infusion of SNP. * indicates significance from control and ** indicates significance from all other treatment groups ($p<0.05$; Student's paired t-test).

In Examples 2, 3 and 4, we used a 30 second infusion of SNP to induce a transient depressor response (less than 1 minute) in order to assess mechanisms involved in homeostatic adjustment, in each case comparing treatment to the respective control response (FIG. 8, Table 3). In control animals, the response was characterized by a depressor response followed by an increase in MAP up to, but not significantly above, the original baseline pressure (2.2±3.53 mmHg, n=30). In contrast, after $\alpha_1$-adrenoceptor antagonism the response to the depressor challenge was altered such that there was a marked overshoot of MAP above baseline during the recovery phase. In some instances MAP took in excess of five minutes to return to baseline following the overshoot. FIG. 8a shows the normal depressor response to a 30 second SNP infusion. This response was unchanged by NOS antagonism (FIG. 8b) and RAS inhibition (FIG. 8c). Overshoot was consistently demonstrated in animals treated with an alpha-adrenoceptor antagonist (FIG. 8d) and those treated with a combination of alpha-adrenoceptor antagonist and NOS antagonist (FIG. 8e), but not in those treated with a RAS inhibitor or NOS antagonist alone. Co-administration of the ETRA SB209670 in the treatment groups demonstrating overshoot abolished this aberrant pressure response (FIG. 8f), indicating that the "overshoot" was an ET-mediated event.

In addition, we characterized the rate of recovery of MAP as determined by the upward slope of the arterial blood pressure trace during a 10 second interval immediately after the onset of recovery (Table 4). The rate of recovery was found to be unchanged in animals treated with alpha-adrenoceptor antagonist, NOS antagonist, and ETRA alone. In contrast, the combination of alpha-blockade and NOS antagonism doubled the magnitude of the recovery slope. The combined antagonism of both endothelin receptors and alpha-adrenoceptors significantly blunted the rate of recovery regardless of whether a NOS antagonist was co-administered.

TABLE 3

Enhancement of Depressor Response to SNP occurs independent of changes in baseline.

| Drug Treatment | Δ MAP (from initial baseline; mmHg) | Change in Vascular Response to SNP |
|---|---|---|
| Terazosin | −28 ± 18.5 | ↑ |
| Hexamethonium | −18 ± 10.0 | ↑ |
| Losartan/Enalarpilat | −38 ± 4.6 | ←→ |

TABLE 3-continued

Enhancement of Depressor Response to SNP occurs independent of changes in baseline.

| Drug Treatment | Δ MAP (from initial baseline; mmHg) | Change in Vascular Response to SNP |
|---|---|---|
| Terazosin/L-NAME/SB 209670 | −26 ± 8.0 | ←→ |
| L-NAME | 36 ± 11.1 | ↑ |

Enhancement of the depressor response to SNP is induced by an agent-specific and pressure-independent mechanism. Despite equivalent or greater pressure lowering in animals with inhibition of the RAS and in animals treated with an ETRA in combination with terazosin and L-NAME (3 mg/kg), there was no enhancement of the vascular response to SNP. In contrast, animals treated with terazosin alone, L-NAME alone or hexamethonium demonstrated enhancement of the depressor response to SNP.

TABLE 4

Overshoot of MAP relative to control response (ΔmmHg) and the rate of recovery (mmHg/sec) following SNP depressor challenge.

| Treatments | Overshoot (mmHg) | Change vs Control | Rate of Recovery (mmHg/s) | Change vs Control |
|---|---|---|---|---|
| L-NAME (n = 7) | −1.6 ± 3.68 | ←→ | 1.2 ± 0.73 | ←→ |
| Los/Enal (n = 8) | 1.6 ± 2.65 | ←→ | 1.4 ± 0.43 | ←→ |
| Los/Enal + L-NAME (n = 8) | 1.6 ± 3.49 | ←→ | 3.3 ± 0.78* | ↑ |
| TRZ (n = 8) | 45 ± 5.19* | ↑ | 1.2 ± 0.42 | ←→ |
| SB 209670 (n = 5) | 0.5 ± 4.98 | ←→ | 1.4 ± 1.00 | ←→ |
| TRZ + SB 209 670 (n = 5) | −3.4 ± 7.77 | ←→ | 0.3 ± 1.03* | ↓ |
| TRZ + L-NAME (n = 5) | 10.1 ± 6.80** | ↑↑ | 2.6 ± 0.51** | ↑ |
| TRZ + L-NAME + SB 209670 (n = 5) | −1.1 ± 7.63 | ←→ | 0.44 ± 0.24* | ↓ |

In the control animals, overshoot following a SNP (10 mg/kg/min) depressor challenge was 2.2 ± 3.53 mmHg (n = 30). The rate of recovery from a SNP (30 mg/kg/min) depressor challenge in control animals was 1.3 ± 0.58 mmHg/s (n = 27). All treatments were maximal blockade, with the exception of the combination TRZ and NOS antagonist groups where 3 mg/kg L-NAME was used. * is significance from control and ** is significance from all other treatment groups (p < 0.05).

Example 7

Assessment of Selectivity of Enhanced Response to Depressor Agents for NO-mimetics Hypersensitivity to NO-mimetics following NOS blockade is shown to be the result of a specific interaction between ET and depressor agents that target the NO pathway. To confirm the specificity of this interaction, dose responses to a variety of depressor agents targeting both NO-dependent and NO-independent pathways were performed before and after maximal NOS blockade with 100 mg/kg L-NAME. One dose of each depressor agent that decreased MAP by approximately 10 mmHg was chosen for analysis. The agents compared were SNP (10 mg/kg/min; 30 s infusion), 8-bromo-cGMP (8-Br-cGMP; 3000 mg/kg/min; cumulative from 30, 100, 300, 1000, 3000 dose response, 2 min infusion, 3 min between doses), bradykinin (30 mg/kg/min; 30 s infusion), $PGE_1$ (10 mg/kg/min; cumulative dose response, 20 min/dose) and INE (0.2 mg/kg/min; 30 s infusion).

Comparison of the depressor responses to SNP, 8-Br-cGMP, PGE1, bradykinin and INE before and after L-NAME revealed that only responses to the depressor agents that target the NO pathway were augmented following L-NAME (Table 5). These results confirm the concept that the augmented depressor response represents an alteration specific to changes in the NO-ET balance.

TABLE 5

NO-selectivity of enhanced depressor responses following maximal NOS blockade with 100 mg/kg L-NAME.

| Depressor Agent | Δ MAP Control (mmHg) | Δ MAP L-NAME 100 mg/kg (mmHg) | Change in Depressor Response |
|---|---|---|---|
| Sodium Nitroprusside (SNP) | −6.63 ± 2.88 | −22.8 ± 12.26** | ↑↑ |
| 8-Br-cGMP | −0.67 ± 2.83 | −26.57 ± 6.76** | ↑↑ |
| Bradykinin | −12.14 ± 4.39 | −17.39 ± 4.47 | ←→ |
| $PGE_1$ | −15.21 ± 5.72 | −15.51 ± 9.74 | ←→ |
| Isopropyl-norepinephrine (INE) | −9.42 ± 7.38 | −10.52 ± 4.04 | ←→ |

The depressor response to various agents after maximal NOS blockade with L-NAME was enhanced only for agents that target NO-dependent pathways. Specifically, the depressor response to bradykinin, $PGE_1$ and INE was unaltered by L-NAME treatment. The depressor response to SNP and 8-Brc-GMP was augmented during L-NAME hypertension.

By antagonizing the SNS effector mechanism, only local adaptive responses remain to respond to the transient depressor challenge. Based on our finding that NO can directly regulate the activity of ET, the infusion of an NO-mimetic would thereby suppress the actions of ET. Once the infusion is stopped, ET activity returns to the previous level, in both control and NOS blocked animals, such that vasoconstrictor tone recovers to pre-infusion levels. Following the infusion of SNP in the alpha-blocked animals, there was a marked overshoot of the MAP, indicating an unopposed contribution of local mechanisms, more specifically ET, in the rapid, but inappropriate, homeostatic regulation. This overshoot was completely prevented by antagonism of endothelin receptors. In addition, we found that graded NO deficiency further exacerbated the ET-dependent abnormality induced by alpha-adrenoceptor antagonism.

The contents of all publications cited in this disclosure are incorporated herein by reference in their entirety.

While there have been shown and described various embodiments of the present invention, it will be obvious to one of ordinary skill in the art that modifications may be made therein without departing from the scope of the invention as it is defined by the appended claims.

We claim:

1. A method of preventing or inhibiting adverse cardiovascular effects associated with administration of a sympathetic nervous system antagonist in a subject, comprising administering to a subject in need thereof a sympathetic nervous system antagonist and an endothelin antagonist.

2. The method of claim 1, wherein the sympathetic nervous system antagonist and the endothelin antagonist are coadministered.

3. The method of claim 1, wherein the sympathetic nervous system antagonist and the endothelin antagonist are administered as a single dosage unit.

4. The method of claim 1, wherein the sympathetic nervous system antagonist is an alpha-adrenoceptor antagonist.

5. The method of claim 4, wherein the alpha-adrenoceptor antagonist is selected from the group consisting of doxazosin, prazosin, terazosin, and phentolamine.

6. The method of claim 1, wherein the sympathetic nervous system antagonist is a ganglionic blocking agent.

7. The method of claim 1, wherein the sympathetic nervous system antagonist is selected from the group consisting of hexamethonium, mecamylamine, clonidine, guanethidine, and reserpine.

8. The method of claim 1, wherein the endothelin antagonist is selected from the group consisting of ABT-627, Bosentan, SB209670, and an NO-mimetic.

9. A method for improving the efficacy of a sympathetic nervous system antagonist, comprising administering to a subject in need thereof a sympathetic nervous system antagonist together with an endothelin antagonist.

10. The method of claim 9, wherein the sympathetic nervous system antagonist and the endothelin antagonist are administered sequentially.

11. The method of claim 9, wherein the sympathetic nervous system antagonist and the endothelin antagonist are coadministered.

12. The method of claim 11, wherein the sympathetic nervous system antagonist and the endothelin antagonist are administered as a single dosage unit.

13. The method of claim 9, wherein the sympathetic nervous system antagonist is an alpha-adrenoceptor antagonist.

14. The method of claim 13, wherein the alpha-adrenoceptor antagonist is selected from the group consisting of doxazosin, prazosin, terazosin, and phentolamine.

15. The method of claim 9, wherein the sympathetic nervous system antagonist is a ganglionic blocking agent.

16. The method of claim 9, wherein the sympathetic nervous system antagonist is selected from the group consisting of hexamethonium, mecamylamine, clonidine, guanethidine, and reserpine.

17. The method of claim 9, wherein the endothelin antagonist is selected from the group consisting of ABT-627, Bosentan, SB209670, and an NO-mimetic.

18. A method of treating prostate cancer or benign prostate hyperplasia (BPH) in a subject, comprising administering to a subject in need thereof a sympathetic nervous system antagonist and an endothelin antagonist.

19. The method of claim 18, wherein the sympathetic nervous system antagonist and the endothelin antagonist are administered sequentially.

20. The method of claim 18, wherein the sympathetic nervous system antagonist and the endothelin antagonist are coadministered.

21. The method of claim 20, wherein the sympathetic nervous system antagonist and the endothelin antagonist are administered as a single dosage unit.

22. The method of claim 18, wherein the sympathetic nervous system antagonist is an alpha-adrenoceptor antagonist.

23. The method of claim 22, wherein the alpha-adrenoceptor antagonist is selected from the group consisting of doxazosin, prazosin, terazosin, and phentolamine.

24. The method of claim 18, wherein the sympathetic nervous system antagonist is a ganglionic blocking agent.

25. The method of claim 18, wherein the sympathetic nervous system antagonist is selected from the group consisting of hexamethonium, mecamylamine, clonidine, guanethidine, and reserpine.

26. The method of claim 18, wherein the endothelin antagonist is selected from the group consisting of ABT-627, Bosentan, SB209670, and an NO-mimetic.

* * * * *